(12) United States Patent
Benson

(10) Patent No.: US 8,303,536 B2
(45) Date of Patent: Nov. 6, 2012

(54) IMPLANTABLE DELIVERY DEVICE

(75) Inventor: James R. Benson, Los Gatos, CA (US)

(73) Assignee: Sunstorm Research Corp., Los Gatos, CA (US)

( * ) Notice: Subject to any disclaimer, the term of this patent is extended or adjusted under 35 U.S.C. 154(b) by 0 days.

(21) Appl. No.: 12/675,970

(22) PCT Filed: Sep. 2, 2008

(86) PCT No.: PCT/US2008/075067
§ 371 (c)(1),
(2), (4) Date: Jan. 22, 2011

(87) PCT Pub. No.: WO2009/029958
PCT Pub. Date: Mar. 5, 2009

(65) Prior Publication Data
US 2011/0112475 A1   May 12, 2011

Related U.S. Application Data

(60) Provisional application No. 60/969,164, filed on Aug. 30, 2007.

(51) Int. Cl.
*A61M 31/00* (2006.01)
(52) U.S. Cl. .............. 604/93.01; 424/422; 424/424
(58) Field of Classification Search .............. 128/260; 424/1.1, 14, 422–424, 473; 428/402.21; 604/8, 93.01, 523, 891.1
See application file for complete search history.

(56) References Cited

U.S. PATENT DOCUMENTS

| 4,320,759 | A  | * | 3/1982  | Theeuwes ............. 604/892.1 |
| 6,063,395 | A  | * | 5/2000  | Markkula et al. ......... 424/422 |
| 6,156,331 | A  | * | 12/2000 | Peery et al. .............. 424/422 |
| 6,165,225 | A  | * | 12/2000 | Antanavich et al. ..... 623/23.72 |
| 6,361,797 | B1 | * | 3/2002  | Kuzma et al. ............ 424/486 |
| 6,756,048 | B1 | * | 6/2004  | Sano et al. .............. 424/426 |
| 2004/0115268 | A1 | * | 6/2004 | Ashton et al. ............ 424/473 |
| 2007/0077273 | A1 | * | 4/2007 | Martin et al. ............. 424/423 |
| 2007/0141107 | A1 | * | 6/2007 | Kutryk et al. ............ 424/423 |
| 2008/0286278 | A1 | * | 11/2008 | Connelly et al. ......... 424/140.1 |

* cited by examiner

*Primary Examiner* — Nicholas Lucchesi
*Assistant Examiner* — Gerald Landry, II
(74) *Attorney, Agent, or Firm* — David W. Maher

(57) ABSTRACT

The invention relates to delivery devices and methods for providing more uniform delivery of agents such as drugs. In some embodiments, a delivery device is provided made of one or more implantable materials having predetermined agent-permeable and agent-impermeable regions and a reservoir containing one or more active agents, either alone or in an acceptable composition, as well as methods of administering one or more agents using such a device. Also provided are methods of equilibrating such devices, so that a steady state of agent delivery can be achieved at or soon after introduction of the device to its intended location of use. Methods of use of such devices to deliver an agent are also provided.

21 Claims, 8 Drawing Sheets

IMPLANTABLE DELIVERY DEVICE

CROSS-REFERENCE TO RELATED APPLICATIONS

This application claims priority to U.S. Provisional Patent Application No. 60/969,164, filed Aug. 30, 2007, which is hereby incorporated by reference in its entirety.

FIELD OF THE INVENTION

The present invention relates to a delivery system for sustained release of active pharmaceutical ingredients or other compounds ("API"; "agents"), either alone or in combination, for prolonged periods of time in humans, animals and other environments. In particular, the present invention relates to an implantable device capable of delivering agents to the body of a mammal or into other environments which benefit from constant or near-constant delivery for extended periods.

BACKGROUND OF THE INVENTION

Controlled release of therapeutic agents has been of considerable interest. Many APIs are rapidly cleared from a patient's or an animal's system, therefore requiring administration of multiple doses of the API in order to maintain therapeutic benefits. Implantable drug delivery devices can obviate the need for repeated dosing and can provide sustained release of the API for prolonged periods.

Many areas of therapeutic drug delivery can benefit from sustained controlled release devices, particularly in chronic or ongoing conditions. For example, arthritis, cancer, epilepsy, AIDS, and conditions necessitating hormone replacement all benefit from continuous release of appropriate drugs.

One particular area in which implantable sustained release devices are of interest is contraception. Interest in contraceptives that could provide unattended, long-term effectiveness has persisted for several decades. In 1966, Dziuk and Cook discovered that steroid hormones passed through polydimethylsiloxane at a low and relatively constant rate. They observed that capsules of that polymer containing estrogen could influence estrus in the ewe for prolonged periods. [Dziuk, P, Cook, B, *Endocrinology* 78 (1966) 208-211]. Segal and Croxatto proposed in 1967 that subdermal capsules of this polymer may serve as the basis for long-term contraception in women. [Segal, Sheldon, *Studies in Family Planning* 14 (6/7) (1983) 159-163]. In 1966, the Population Council, a non-profit organization located in New York City, began formal studies embodying this concept. After many years of study, a commercial product termed "Norplant®" was developed.

The original Norplant® product consisted of six silicone capsules containing levonorgestrel ("LNG"), a synthetic hormone known to be effective as a contraceptive. These six capsules were inserted subdermally, usually in the upper arm of patients. Amounts of levonorgestrel passed through the walls of the capsules and subsequent systemic distribution of this hormone was shown to provide effective contraception. However, there were significant side effects associated with use of levonorgestrel in this manner.

Although most women tolerated the device well, a significant percentage discontinued the program during the first year of use. [Coutinho, et al., *Contraception* 18 (4) (1978) 31.5-333; Coutinho, et al., *Contraception* 18 (4) (1978) 335-353; Diaz, et al. *Contraception* 25 (5) (1982) 447-456; Goldzieher, J, Fotherby, K, Eds., *Pharmacology of the Contraceptive Steroids*, Raven Press (New York) 1994]. Most discontinuations were due to menstrual irregularities, although other side effects were reported. For those women who tolerated the side effects during the first year of use, most reported a decline in severity of disturbances after twelve to eighteen months. [Diaz, S, Pavez, M, Robertson, D. Croxatto, H. *Contraception* 19 (6) (1979) 557-573; Shaaban, M, Salah, M, Zarzour, A, Abdullah, S, *Studies in Family Planning* 14 (6/7) (1983) 163-169]

Release rates and drug release profiles were studied. After initial insertion the average release rate of levonorgestrel is approximately 80 µg per day. This declines over twelve to eighteen months and reaches a relatively steady release rate of approximately 30 µg per day for the remainder of the time of use ["Norplant® Release Rate", *The Population Council* (1991)]. A threshold dose of 24 µg per day of levonorgestrel was found to be required for contraception, and in another study, a dose of 18 µg per day of levonorgestrel was required for acceptable effectiveness. It is generally acknowledged that a release amount of approximately 30 µg per day of levonorgestrel will prevent conception for most women and, therefore, any release of the steroid above approximately 30 µg per day is unnecessary for efficacy. It is conceded that the relatively high release of levonorgestrel during the first twelve to eighteen months following insertion of Norplant® is likely responsible for adverse symptoms reported by many women. [Primiero, F. and Beliagiano, G, in Goldzieher, J, Fotherbv, K, Eds., *Pharmacology of the Contraceptive Steroids*, Raven Press (New York) 1994, p. 173]. This elevated release of a drug following administration is known as a "burst".

To understand the reason for the burst and subsequent decline of release rate until a relatively steady state is achieved, it is necessary to examine the mechanism of interaction between the steroid hormone and the polydimethylsiloxane capsule. Once crystals of levonorgestrel are loaded into the capsule, they begin to dissolve in the capsule walls and migrate to the outer surface. By the time the manufactured capsules are ready for implantation, levonorgestrel has saturated the polymer and accumulated in the walls. Once the saturated capsules are inserted into a patient, there is a rapid release of the drug, resulting in a burst.

Following the burst, water from the patient's body begins to migrate slowly through the walls of the capsule to its interior. This process is very slow and it takes some months before significant amounts of water accumulate in the capsule chamber [Robertson, Dale, in Zatuclrni, G, Goldsmith, A, Shelton, J, Sciarra, J, *Long Acting Contraceptive Delivery Systems*, Harper Row (Philadelphia) (1983)]. As water reaches the capsule chamber, levonorgestrel crystals begin to dissolve in this accumulated water. The walls of the capsule become saturated with water containing levonorgestrel and transport of levonorgestrel correspondingly becomes limited by its solubility in water. It is at this point, approximately eighteen months after implantation of the capsules, that release of levonorgestrel attains equilibrium and a relatively constant amount of 30 µg per day is released.

There is a need in the art for devices which provide more uniform delivery of chemical agents, which exhibit a reduced burst phase, and for methods of reducing or eliminating the burst associated with delivery devices.

SUMMARY OF THE INVENTION

The invention relates to delivery devices and methods for providing more uniform delivery of agents such as drugs. In some embodiments, a delivery device is provided made of one or more implantable materials having predetermined agent-permeable and agent-impermeable regions and a reservoir containing one or more active agents, either alone or in an acceptable composition, as well as methods of administering one or more agents using such a device. Also provided are methods of equilibrating such devices, so that a steady state of agent delivery can be achieved at or soon after introduction of the device to its intended location of use. Methods of use of such devices to deliver an agent are also provided.

DETAILED DESCRIPTION OF THE INVENTION

Figure 1:
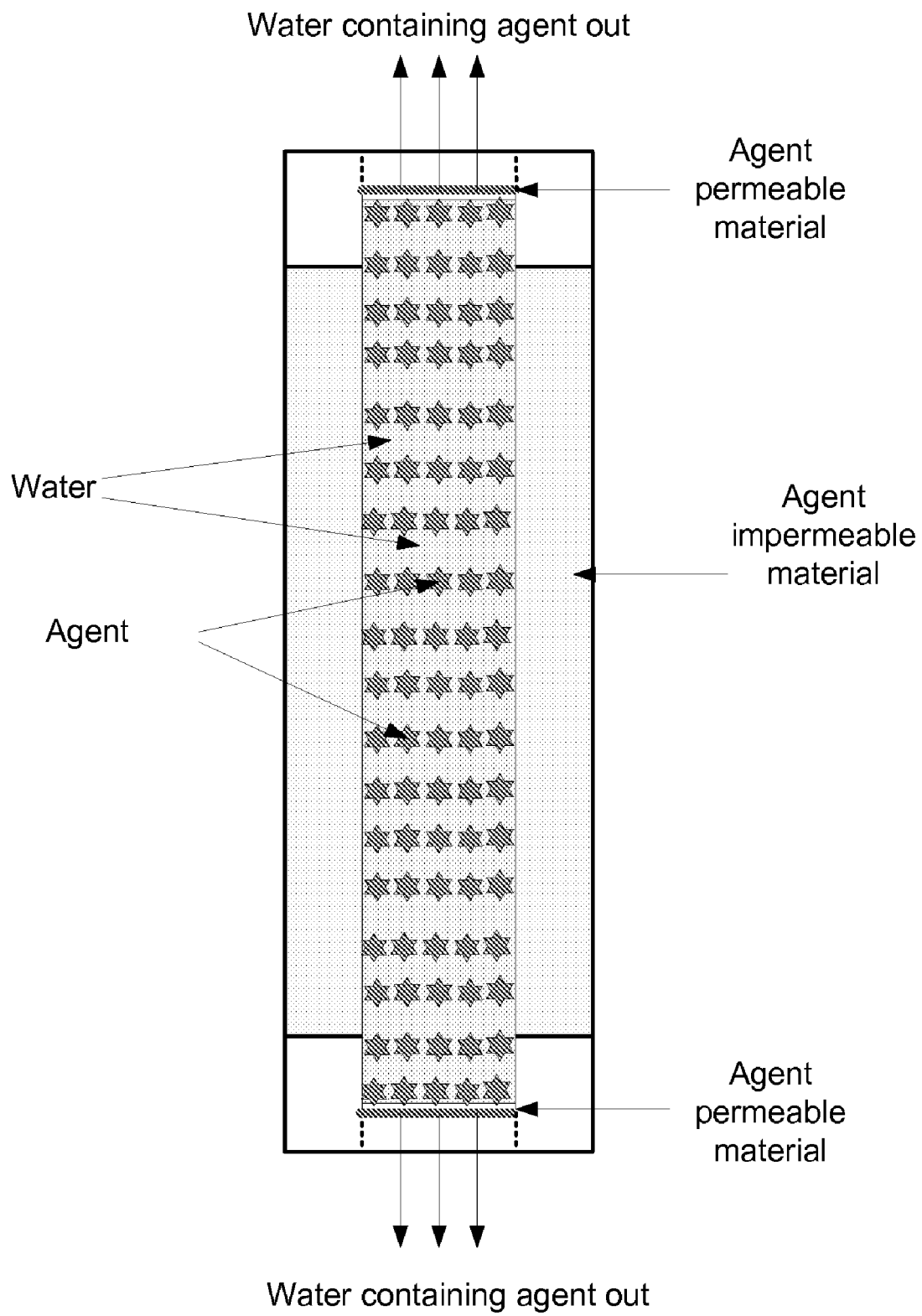
FIG. 1 depicts a cylindrical delivery device in accordance with the invention.

The Norplant® design resulted in a large burst of levonorgestrel following insertion of the implants. This large burst peaked after insertion and caused levonorgestrel to remain at levels higher than required for contraceptive benefit for about eighteen months. Once crystals of levonorgestrel are loaded into the Norplant® capsule, they begin to dissolve in the capsule walls and migrate to the outer surface. By the time the manufactured capsules of that device were ready for implantation, levonorgestrel has saturated the polymer and accumulated in the walls. Once the saturated capsules were inserted into a patient, there was a rapid release of the steroid, resulting in a burst. This results from the permeability of the entire Norplant device to levonorgestrel, along with the fact that the contents of the device are not at equilibrium with respect to their ultimate target.

The extant invention is simple yet particularly useful because it allows great flexibility and precision in controlling the amount of API release as a function of time. Desirably, the devices provided herein exhibit zero-order or near zero-order release of agents at therapeutic or otherwise desired levels for extended periods of time.

"Zero order release" is a term used to describe a constant amount of drug being released per unit time. It is considered highly desirable to achieve zero-order release for many medications, including levonorgestrel, because zero-order release avoids the burst of medication into patients and because a constant blood level is maintained for an extended period to optimally provide therapeutic benefits.

A device is provided that is made of one or more implantable materials comprising two types of predefined regions: an agent-impermeable region (which may comprise one or more different materials); and one or more agent-permeable regions (which also may comprise one or more different materials). The device also comprises one or more reservoirs used for retaining an active ingredient or ingredients, which may be therapeutic agent(s).

The device may take any suitable shape which permits an agent reservoir to be surrounded by an agent-impermeable region while the agent reservoir is in contact with one or more agent-permeable regions through which the agent can be released. The device may be a disk, rod, prism, or cube. In some embodiments, the device may have one dimension significantly longer than the others, and may be two-fold, three-fold, four-fold, five-fold, 10-fold, or more longer in that dimension. In some embodiments, the device has a length in the range of 1-500 mm.

Where the device is a disk, a rod or is rod-like, the cross section of the device may be an oval, ellipse, circle, rectangle (including square), triangle, or any other regular polygon, may have an irregular shape. In particular embodiments of interest, the device is provided in the form of a cylindrical rod, having a circular cross-section.

The agent-permeable material is of a type, thickness and area chosen to permit efflux of the agent through the region(s) at the desired rate. Although the materials forming the device are referred to as agent-permeable and agent-impermeable, the agent-permeable region(s) permit a slow, sustained release of agent at a consistent rate for most of the useful lifetime of the device. The agent-impermeable region(s) may permit limited transfer of agent at a much lower rate that does not significantly alter the amount of agent released. Such impermeable regions thus do not permit more than 25% of release of the total agent released by the device for a given time period, which may be the period of intended release or zero-order or near zero-order release. Preferably, the agent-impermeable regions do not release more than 20% of the agent released, more preferably less than about 15%, still more preferably less than 10%, and most preferably 5% or less of the total agent released. In some embodiments, no significant agent is released from the agent-impermeable regions (1% or less).

Exemplary materials which may be used as agent-impermeable in particular settings include ultra-high molecular weight polyethylene, polyanhydrides, polyacrylates, polyurethanes, polytetrafluorethylene, hydrophobic polyamino acids, polypropylene, polyvinylalcohol, polycarbonate, titanium, stainless steel, and polyesters. The choice of agent-impermeable material can be influenced by the agent to be delivered and the location of implantation. In some embodiments, one or more imperfections can be introduced into the agent-permeable region(s), and/or into the agent-impermeable region(s), in accordance with the teachings herein, which do not significantly alter the agent delivery, and may be useful in some cases to accelerate equilibration.

Exemplary materials which may be used as agent-permeable in particular settings include polydimethylsiloxane, other siloxanes, poly(ethylvinyl acetate), porous membranous materials, including cross-linked polyvinyl alcohol, polyolefins, polyvinyl chlorides, cross-linked gelatins; regenerated, insoluble, non-erodible cellulose, acylated cellulose, esterified celluloses, cellulose acetate propionate, cellulose acetate butyrate, cellulose acetate phthalate, cellulose acetate diethyl-aminoacetate, polyurethanes, polycarbonates, and microporous polymers formed by co-precipitation of a polycation and a polyanion, modified insoluble collagen, perforated impermeable materials (e.g. polytetrafluoroethylene), woven materials (e.g., polyester), filtration materials, and nylon.

Other materials that may be employed in the device include polyethyl hexylacrylate, polyvinyl chloride, polyvinyl acetals, plasticized ethylene vinylacetate copolymer, polyvinyl acetate, ethylene vinylchloride copolymer, polyvinyl esters, polyvinylbutyrate, polyvinylformal, polyamides, polybutylmethacrylate, plasticized polyvinyl chloride, plasticized nylon, plasticized soft nylon, plasticized polyethylene terephthalate, natural rubber, polyisoprene, polyisobutylene, polybutadiene, polyethylene, polyacrylonitrile, cross-linked polyvinylpyrrolidone, polytrifluorochloroethylene, chlorinated polyethylene, poly(1,4'-isopropylidene diphenylene carbonate), vinylidene chloride, acrylonitrile copolymer, vinyl chloride-diethyl fumerale copolymer, ethylene-propylene rubber, silicone-carbonate copolymers, vinylidene chloride-vinyl chloride copolymer, vinyl chloride-acrylonitrile copolymer, vinylidene chloride-acrylonitride copolymer, gold, and platinum.

The agent permeable regions may be found in any discrete area of the device, and may be on the surface of the device, or in recessed areas surrounded by impermeable material. In some embodiments, the agent-permeable regions may be located at one or more ends of projections on the device. Where the device takes a cylindrical, prism or rod-like shape, in some embodiments, the permeable regions may take the form of one or more ends of the device.

Where the device takes the form of a disk, the disk surfaces may comprise the permeable region(s), and the disk edge can comprise the agent-impermeable region.

The components of the device may be manufactured and assembled using techniques known in the art. Thus, individual components may be prepared by molding, machining, extruding, stamping, cutting, or other methods which produce suitably uniform components. The components may be assembled using known techniques, including sealing, adhesives, welding, ultrasonic treatment, heating, coating, press-fitting, dipping, spraying, dropping, brushing, printing, or other methods. Multiple assembly steps may be performed using the same or different techniques.

In some embodiments, the device takes the form of one or more generally cylindrical rods having an axial compartment or reservoir for containment of an agent or agents. The rods have a cylinder made of an agent-impermeable material, and one or two caps on part or all of the cylinder end(s) made of an agent-permeable material. Sustained release can be attained from cylinders whose walls are impermeable to drugs if the incorporated agents are allowed to pass preferentially through one or both of the cylinder ends that are capped with an agent permeable material. Zero-order release or near zero-order release can be attained if the agent within the chamber of the cylinder is maintained at a sufficiently high concentration relative to the outside environment. Instead of using thick membranes of polydimethylsiloxane at cylinder ends, one can use a thinner membrane of polydimethylsiloxane or other appropriate polymer membrane having an associated faster diffusion rate. This design can achieve the same delivery rate as cylinders having a larger diffusion area but thicker membrane. This is possible because the thinner membrane allows much faster equilibrium between the agent contained in the reservoir and the external environment. The device may be pre-equilibrated with water or a solution resembling extracellular-fluid prior to insertion into the patient or animal.

In some embodiments, the agent-impermeable cylinder comprises titanium or ultra high molecular weight polyethylene.

In some embodiments, the end cap is molded from polydimethylsiloxane wherein the membrane and end cap body are molded as a single unit. The single unit end cap can be made to snap-fit onto the cylinder body by methods known to those skilled in the art such that it does not dislodge when in use.

In some embodiments, a thin membrane of polydimethylsiloxane is used to cover the ends of a cylindrical rod that can be perforated once or multiple times with a perforating device such as a steel wire of fixed dimensions. Silicone is known to "re-seal" itself when small perforations occur. However, these perforations create imperfections that allow faster diffusion of agents through the thin membrane. Adjustment of the number of perforations and diameter of the perforating device provides another method for controlling the agent diffusion rate.

In some embodiments, thin membranes of polydimethylsiloxane covering the ends of a cylindrical rod can be perforated once or multiple times with a laser that can produce precise imperfections of varying dimensions. The silicone membrane will re-seal itself as long as the laser does not produce too wide imperfections, which can be controlled through beam width and focusing techniques, as known in the art. As with the perforations mentioned above, these laser-created imperfections allow faster diffusion of agents than occurs through unperforated membranes. Adjustment of the number and diameter of the laser-created imperfections becomes another means for controlling the desired diffusion rate. The optimum conditions for creation of laser-created imperfections must be determined for each type of agent and each type of polydimethylsiloxane or other material used.

In some embodiments, a membrane of poly(ethylvinyl acetate) can be substituted for polydimethylsiloxane for the agent permeable region(s).

In some embodiments, the size of the imperfections in the membrane can be increased to create one or more holes of appropriate dimensions to allow diffusion of agents at the desired diffusion rate.

In some embodiments, porous polymer sheets can be used as membranes covering the ends of the cylinders.

In some embodiments, polymer sheets that would normally be impermeable to the agent of interest can be made permeable by creating imperfections or holes with a penetrating device or laser as described above.

It is recognized that the ability of an agent to permeate a given material will vary with the properties of the agent (including lipophilicity), the thickness and grade of the material, as well as its composition. Thus, in some settings with certain agents, a material may act as an agent-permeable material, while in other settings with a different agent, the material may be used as an agent-impermeable material. Similarly, a material having some permeability for an agent can be used to form agent-permeable and agent-impermeable regions of the same device, with a thicker form of the material having a lower diffusion rate being used in the agent-impermeable regions, and thinner forms of the material with higher diffusion rates being used in the permeable regions.

According to Fick's Law, the amount of material diffusing through a membrane is proportional to the area of a circular membrane. Since this area is proportional to the square of the diameter, it is possible to precisely select the desired amount of API released per unit time by making relatively small changes in membrane (and cylinder) diameter.

"Cross-sectional diameter" as used herein means, in the case of a circular cylinder, the diameter of the cross section taken at right angle to the axis ("right section" hereafter). In the case of a prism, the "cross-sectional diameter" means the length of the largest diagonal in the right section. In the case of an elliptical cylinder the "cross-sectional diameter" means the length of the major axis in the right section. "Axial length" as used herein refers to the distance between the two ends in axial direction of drug formulation.

The device reaches its initial steady state of release when there is no more than a 10% change in the average amount of agent emitted per day within a 10 day period. At this point the device has equilibrated sufficiently to achieve continuous release. The device then subsequently desirably exhibits zero-order or near zero-order release for the intended useful lifetime. The intended lifetime may be any period over which such a device may be efficaciously used, and varies depending on the type of use, condition of the location or patient into which implantation is intended, and other factors. In medical settings, for transient conditions, the device may be used for as little as a week. More typically, such device will be used for at least a 30-day period of agent delivery, and may be used for 60 days, 90 days, 120 days, 180 days, 365 days, one and a half years, two years, three years, and five years or more.

The release of agent from the device will exhibit zero-order or near zero-order release when the concentration of agent within the agent reservoir is maintained at or near a particular concentration. This can be accomplished when efflux does not significantly affect the concentration within the reservoir for the intended delivery period, as the internal concentration in part controls the rate of efflux. This can also be achieved when the agent dissolved in the solution is replenished during delivery, for example by dissolving previously undissolved agent within the reservoir that is in contact with the solution (e.g., solid agent).

In some embodiments, for low solubility compounds, when external fluids fully fill the chamber within the capsule, the chamber may contain a saturated solution of agent plus external fluid, depending upon the solubility of agent. Under these conditions, a condition known as "zero-order release" will occur as the saturated solution diffuses through the permeable region(s). This constant release rate will continue as long as the solution contained within the chamber remains saturated and the local temperature remains relatively constant.

By "zero-order release" is meant a rate of release that provides an average release curve whose slope varies no more than 10% during the effective lifetime that the device is used for delivery. It is recognized that some minor variability in release of agent, and in measurement of that release, occurs even during zero-order release, and does not alter the overall average zero-order delivery. Use of multiple separate devices to achieve the total desired delivery can further dampen the effects of normal fluctuations from any one device.

"Near zero-order" is meant a rate of release that provides an average release curve whose slope varies no more than 25% during the effective lifetime that the device is used for delivery. Preferably devices exhibiting average zero-order or near zero-order release vary no more that 50% and preferably no more than 25%, from their initial release steady state of release during the period desired for efficacy of the application. Preferably, the device may provide no more than a 20% change in its average delivery rate, and more preferably a 15% percent or less change, over a period of 10-30 days or more.

In some embodiments, an amount of agent is loaded into the inner chamber of the device such that when external fluids completely fill the chamber, a steady state concentration of solution of agent plus external fluids ensues. This will permit near zero-order release of agent for the desired period of time. In some embodiments, where the solution is saturated or where the internal concentration is high in relation to the efflux rate, zero-order release occurs for an extended period.

Many areas of therapeutic drug delivery can benefit from sustained controlled release devices, particularly in chronic or ongoing conditions. Exemplary agents which may be employed in such a device for humans and animals include APIs used for treating arthritis, cancer, epilepsy, treatment of AIDS, conditions necessitating hormone replacement, behavioral disorders, psychotic disorders, treatment of chronic and neuropathic pain, morphine and other opiates, treatment of addiction and other chemical dependencies, treatment of insulin production disorders, administration of steroids or other pharmaceuticals to livestock, antibiotics, alkylating agents treatment of parasitic and fungal infections, treatment of hypertension, arrhythmia, and other cardiovascular disorders, anti-emetics, anti-rejection drugs, anti-inflammatory drugs (e.g., ketorolac), steroid hormones, contraceptive hormones including levonorgestrel, anti-epileptics, chemotherapeutic agents, male contraceptive hormones, and treatment of benign prostate hypertrophy. The agents may be chemical or biological in nature. In some embodiments, the agent may be selected from cytokines, hematopoietic factors, hormones, growth factors, cell adhesion factors, enzymes, blood coagulating factors, proteins involved in bone metabolism, and antibodies. Combinations of agents may be used.

Of particular interest are lipophilic drugs and drugs of low aqueous solubility, including steroid hormones. Steroid hormones of particular interest include those desired for long-term treatment, for example anti-androgen therapy treatment of prostate cancer, and for contraceptive methods. One steroid hormone of particular interest is levonorgestrel.

Furthermore, in some embodiments, equilibrium of devices provided by this invention is attained during manufacture, unlike the Norplant® device wherein equilibrium is only attained after implantation. The device may be equilibrated by contacting the device with a solution useful in establishing a steady state concentration of agent within the device, such that a more uniform rate of release can be obtained upon subsequent implantation into its location in use. Exemplary solutions which may be used include water and iso-osmotic solutions, for example phosphate-buffered saline. Other solutions which may be used to equilibrate the delivery device can be any medium used to replicate the environment into which the device is introduced. For example, media used to culture cells from the organism can be used to equilibrate the device. Where the intended use is in a mammal, a mammalian cell culture medium may be used. Exemplary mammalian cell culture media include Ham's F10, Ham's F12, Eagle's Medium, Dulbecco's-modified Eagle's Medium, RPMI-1640, Minimum Essential Medium, essential salts, and combinations thereof. Such media may be used with or without serum, plasma, combinations thereof, and/or a substitute therefor; media comprising potential antigens such as proteins should be from the intended host organism, and preferably are recombinant or from a defined donor population in order to minimize any risk of infection.

After equilibration, the device may be isolated from the equilibration device, and may be packaged, optionally in a pre-equilibrated solution. In this manner, a pre-equilibrated device having a steady-state concentration is provided prior to administration or implantation. The device can then maintain a steady-state of delivery in use, which may be zero-order or near-zero-order delivery.

The original Norplant® cylinder yielded approximately 5 μg LNG per day per cartridge. Since 18-30 μg per day of LNG is necessary for contraception, six cylinders were implanted into patients. The examples discussed above showed LNG release up to about 10 μg per day per cylinder. Consequently, fewer implants of this particular design can achieve effective human contraception; for example, 2-4 devices as shown in the examples can provide a therapeutic dose for an extended time, as compared to the six cylinders used in the Norplant® cylinder. Adjustment of the parameters described herein in the cylinder design can influence the amount of agent released per unit time; by altering the parameters described, it is possible to produce a single device [cylinder] that releases the required 30 μg per day.

The drug delivery system of the present invention may be administered to a mammal via any route of administration known in the art. Such routes of administration include intraocular, oral, subcutaneous, intramuscular, intraperitoneal, intranasal, dermal, into the brain, including intracranial and intradural, into a joint, or directly into a tumor. In addition, one or more of the devices may be administered at one time. The drug delivery system may be administered for a sufficient period of time and under conditions to allow treatment of the disease state of concern.

For localized drug delivery, it may be desirable to implant the device(s) at or near the site of action. This is the case for devices of the present invention used in treating ocular conditions, primary tumors, rheumatic and arthritic conditions, and chronic pain.

For systemic relief, it may be desirable to implant the devices subcutaneously, intramuscularly, intraarterially, intrathecally, or intraperitoneally. This is the case when devices are to give sustained systemic levels and avoid premature metabolism. In addition, such devices may be administered orally.

The invention further relates to a method for treating a mammal to obtain a desired local or systemic physiological or pharmacological effect. The method includes administering the drug delivery system to the mammal and allowing the agent to pass through the agent-permeable region(s) to contact the mammal. The term administering, as used herein, means positioning, inserting, injecting, implanting, or any other means for exposing the device to a mammal. The route of administration depends on a variety of factors including type of response or treatment, type of agent, and preferred site of administration.

EXAMPLES

The following examples are set forth so as to provide those of ordinary skill in the art with a complete description of how to make and use the present invention, and are not intended to limit the scope of what is regarded as the invention. Efforts have been made to ensure accuracy with respect to numbers used (e.g., amounts, temperature, etc.) but some experimental error and deviation should be accounted for. Unless otherwise indicated, parts are parts by weight, temperature is degree centigrade and pressure is at or near atmospheric, and all materials are commercially available.

Example 1

Manufacture of Delivery Devices

Levonorgestrel ("LNG") was chosen as an API. A design used for sustained controlled release of LNG is shown in FIG. 1. LNG is loaded into the interior reservoir of a cartridge, the body of which is composed of ultra high molecular weight polyethylene. Water is added to the reservoir to accelerate equilibration time. The end caps are #316 stainless steel and these caps hold into place a membrane of polydimethylsiloxane. Polydimethylsiloxane membranes were obtained as a gift from AART, Inc. (Reno, Nev.). Two composition types were utilized: "50A" and "35A". Table 1 summarizes the materials used.

TABLE 1

Silicone membranes used

| Cylinder Reference | AART Silicone Designation | Thickness |
| --- | --- | --- |
| SS-01 | 50A | 0.005" |
| SS-03 | 50A | 0.002" |
| SS-04 | 35A | 0.006" |
| SS-05 | 35A | 0.005" |

Prototype cylinders were manufactured, filled with 35 mg LNG and assembled. The cylindrical bodies were constructed of ultra high molecular weight (UHMW) polyethylene (PE) and the end caps were machined using #316 stainless steel. The cylinders were assembled by first placing one end cap and membrane over one end of the cylinder. LNG was added to each cylinder using a small funnel constructed for the purpose. Each cylinder was weighed to confirm the presence of 35 mg of LNG. Water was added to fill the remaining space within the cylinder reservoir and a second end piece/membrane was affixed into place over the remaining open end. To construct the circular membranes, a cutting die was machined and used to cut disks from the sheets of silicone described above.

Figure 2:
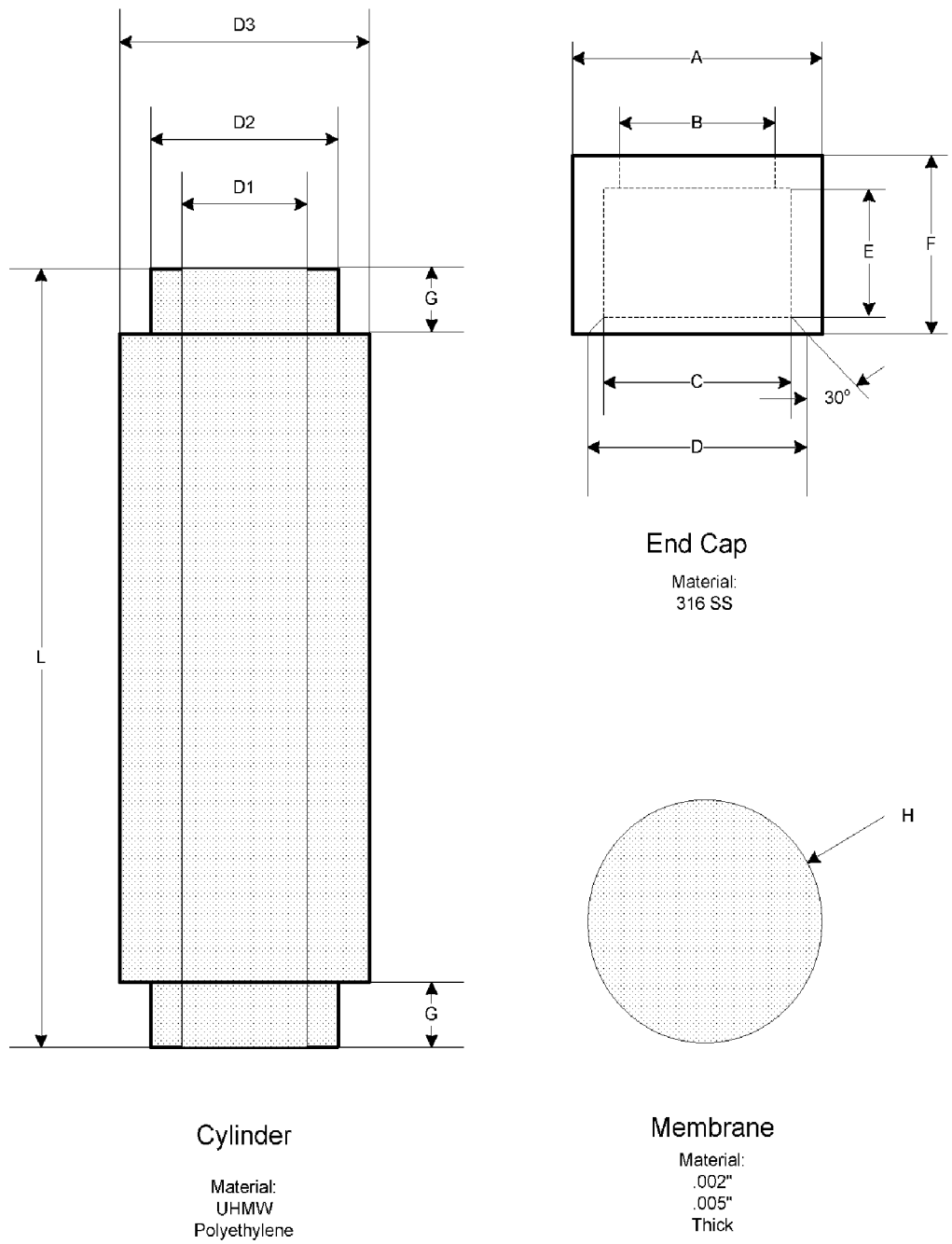
FIG. 2 provides a schematic illustration of one embodiment of a cylindrical delivery device in accordance with the invention. An ultrahigh molecule weight polyethylene is used for the agent-impermeable cylinder body. Stainless steel machined end caps are placed atop a membrane disk of polydimethylsiloxane, and press fit onto the cylinder body, fixing the disks in place. The agent is placed into the agent reservoir prior to sealing the device.

An engineering drawing for this particular design is shown in FIG. 2. Specifications are summarized in the tables below:

TABLE 2

End Cap Dimensions

| Dim | A ±.001 | B ±.002 | C +.0004 −.0000 | D | E +.003 −.000 | F +.003 −.003 |
| --- | --- | --- | --- | --- | --- | --- |
| −01 | .130 | .080 | .1150 | .121 | 0.100 | 0.130 |

TABLE 3

Cylinder Dimensions

| Dim | D1 +.003 −.000 | G +.003 −.000 | L |
|---|---|---|---|
| −01 | .080 | .105 | 1.25" |

TABLE 4

Membrane Dimensions

| Dim | H +.000 −.003 |
|---|---|
| −01 | φ.116 |

At equilibrium, the inner chamber of the cylinder is filled with water saturated with levonorgestrel (see FIG. 1). Neither the levonorgestrel nor the saturated aqueous solution permeates the walls of polyethylene. Instead, the saturated solution can only diffuse through the thin membranes found at the cylinder ends, resulting in release of a constant amount of steroid per unit time.

The device of the invention does not exhibit a burst effect through the membrane-permeable region. Since the membrane affixed to each cylinder end is very thin and since water is added to the chamber containing the steroid at the time of manufacture to create a saturated solution of LNG, equilibrium time is sufficiently low that it can be carried out during manufacture of the device and before implantation into patients.

Example 2

Equilibration of Delivery Devices and Measurement of Agent Delivery

Measurement of LNG released from individual cartridges was carried out by Bay Bioanalytical Laboratory, Inc. (Hercules, Calif.). Levonorgestrel was obtained from Sigma. A prepared kit for phosphate buffered saline (PBS) was also obtained from Sigma. The pH 7.4 PBS contained 0.01 M phosphate, 0.138 M sodium chloride, and 0.0027 M potassium chloride.

Cylinders each containing 35 mg LNG were suspended in test tubes containing 10 mL or 25 mL PBS as described above. A small 10 mm stirring magnet was placed at the bottom of each test tube to continuously stir the PBS. A nylon thread was tied around the cartridge and fixed to the top of the test tube to prevent the cartridge from contacting the magnet. Test tubes were capped, and placed above a magnetic stirrer in an oven at 37° C.

The PBS solutions were initially refreshed approximately every seven days, then twice per week. Prior to taking of samples to determine the amount of LNG released, the test tube was emptied of PBS, fresh PBS was added, and placed again in the 37° C. oven. A 1.5 mL sample was taken 24 hours thereafter and set aside for analysis.

Figure 3:
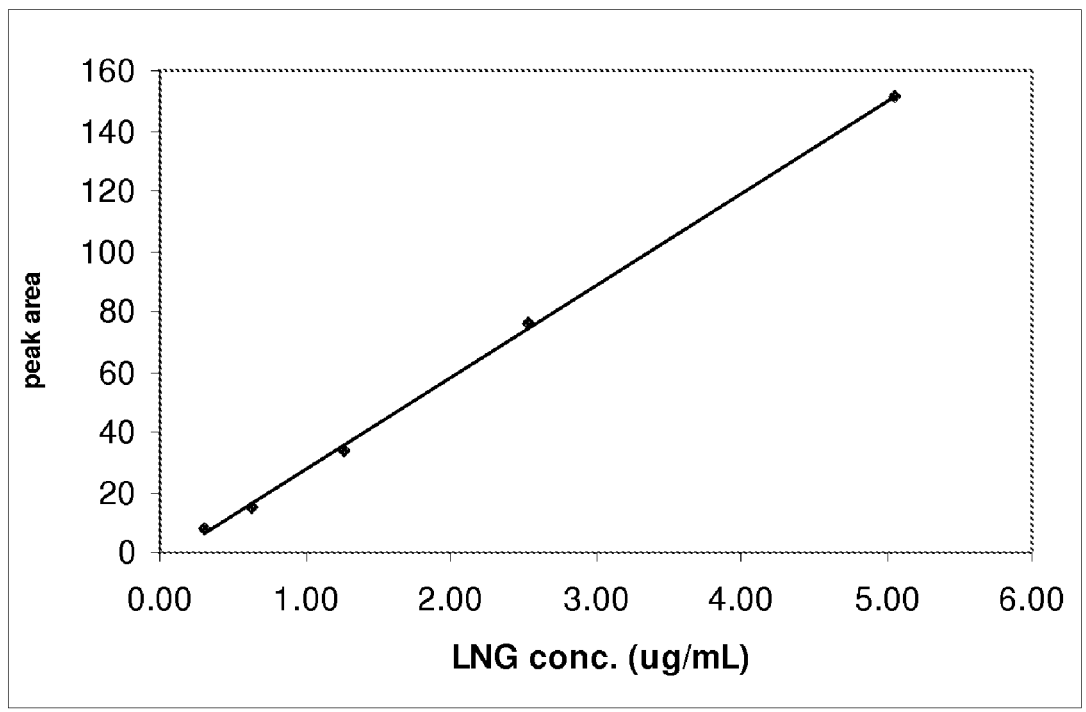
FIG. 3 depicts a calibration curve used to determine the amount of levonorgestrel released from the delivery devices tested in the examples.

A solution containing 1 mg/mL LNG in methanol was diluted to 10 μg/mL with water. This stock solution was kept at −20 C when not in use. A five point standard calibration curve (0.3 μg/mL LNG-5.0 μg/mL LNG, corresponding to a release of 3 μg/day-50 μg/day) was prepared from this stock solution each day that samples were analyzed. The calibration curve and all analyses were accomplished using an Agilent model 1100 HPLC, monitored at 240 nm, with a C18 column (Higgins Analytical, 4.6×300 mm). Samples were processed using an eluent flow rate of 2 mL/min at room temperature. The eluent used was 40% acetonitrile in water, containing 0.1% trifluoroacetic acid. Injected sample size was 100 μL. Absorbance values associated with released LNG in the various samples were compared with the standard curve and were recorded as μg LNG released per day. A standard calibration curve is shown in FIG. 3.

Cylinders were prepared in triplicate for most configurations studied. Release profiles were obtained by averaging the measured values for individual cartridges, excluding outliers. Outliers were identified based upon substantive deviation from adjacent data points Monitoring was stopped in the event a cartridge began leaking. Release values prior to the leakage were averaged with the other cartridges in the group.

An artifact appeared in some LNG release profiles that showed initially elevated levels of LNG lasting for varying amounts of time, up to about twenty days. It was determined that this artifact resulted from handling cartridges during the filling procedure, as the cartridge first prepared did not exhibit this phenomenon. Dust particles of LNG were inadvertently transferred to the external surface of subsequently filled polyethylene cylinders. The hydrophobic nature of LNG caused relatively strong adherence to those surfaces, making dust particles difficult to remove by washing with water. A clean surface was assumed to be reached when measured values of LNG stabilized. More rigorous cartridge-filling procedures can reduce or avoid this phenomenon. Alternatively, surface cleaning procedures can be used. As an example, sonication was found to remove excess surface-deposited compound from the cartridges.

It was found that an initial equilibration period in PBS or water was needed before zero-order equilibrium of each prototype cartridge was achieved. Although there may be other factors involved, this characteristic is presumed to be due to air trapped in the cylinders during manufacturing of the prototypes. In this case, equilibrium is not attained until all trapped air diffuses from the cartridge interior and is replaced by water or PBS. At this point, water within the cartridge chamber has been saturated with LNG and this saturated solution begins to diffuse from membranes at both ends of the cartridge. Zero order release is achieved at this point. The time to reach this zero-order equilibrium varied from about sixty to about ninety days for the various silicone membranes utilized.

The equilibrium time can be further reduced by means known to those skilled in the art. For example, a vacuum pump can be used to remove air trapped in the cylinders and replace this with water through soaking of the cylinder.

FIGS. 4-8 demonstrate release profiles of various device designs.

Figure 4:
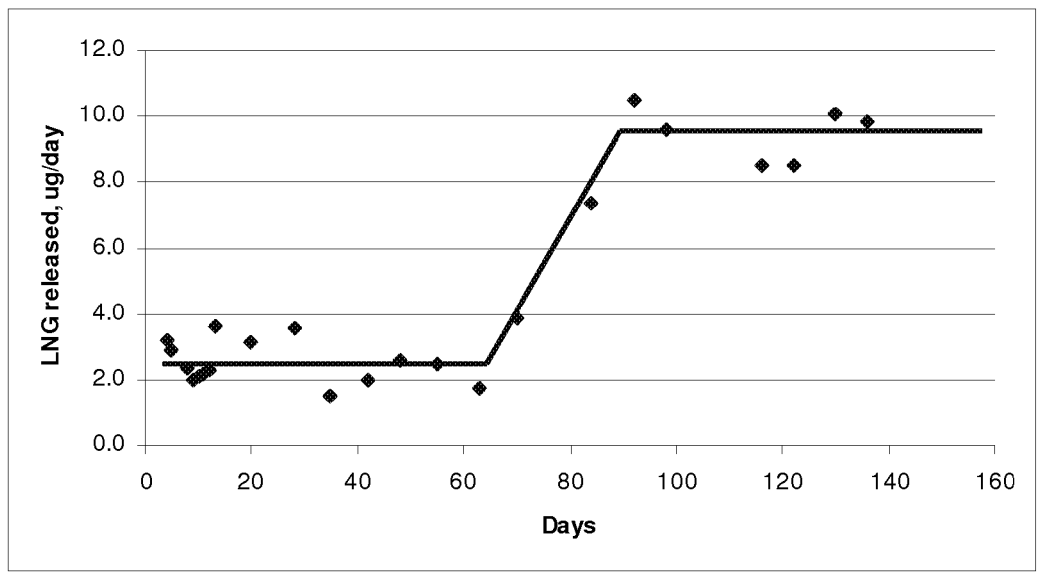
FIG. 4 illustrates the release profile of one embodiment of a delivery device using an SS-01 cylinder and type 50A silicone membrane 0.005" thick as the agent-permeable regions.

FIG. 4 illustrates the release profile of the SS-01 cylinder that utilizes type 50A silicone membrane 0.005" thick and demonstrates the equilibration time necessary for that particular cylinder. With this configuration and filling procedure, it appears to take about ninety days before external water has permeated the cylinder and completely filled the interior cavity. At this point, both agent-permeable membranes are in full contact with water saturated with LNG and the cartridge begins displaying near zero-order release of the LNG.

Figure 5:
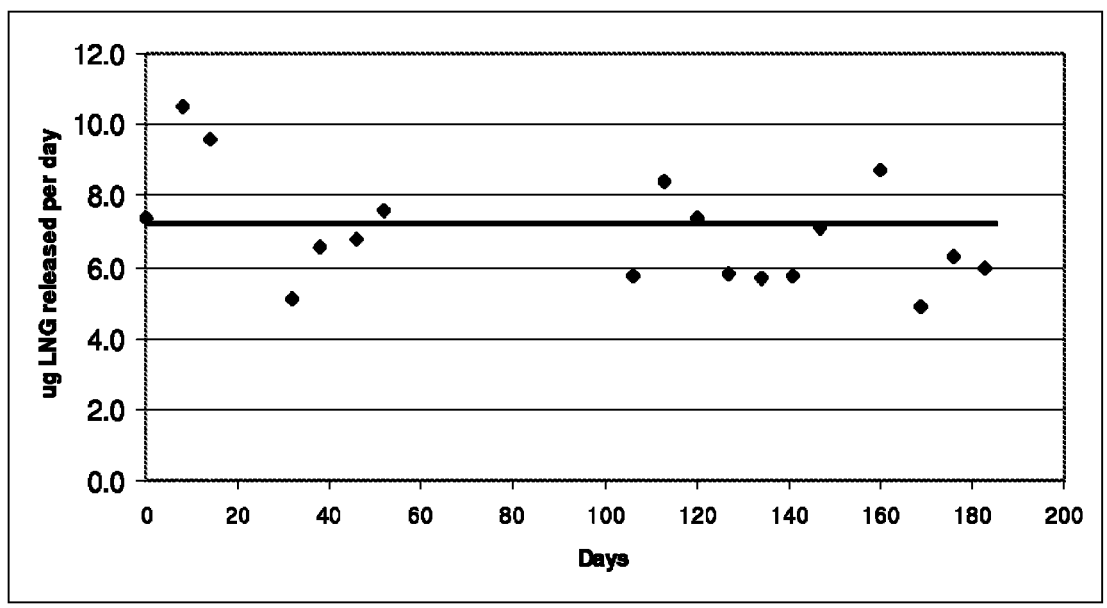
FIG. 5 illustrates the release profile of the SS-01 cylinder after equilibrium was reached. The zero time point corresponds to the equilibrium condition. Equilibrium was obtained after 85 days of soaking and subsequent LNG release values were 7-8 µg/day.

FIG. 5 illustrates the release profile of the SS-01 cylinder after equilibrium was reached. The zero time point corresponds to the equilibrium condition. Equilibrium was obtained after 85 days of soaking and subsequent LNG release values were 7-8 μg/day.

Figure 6:
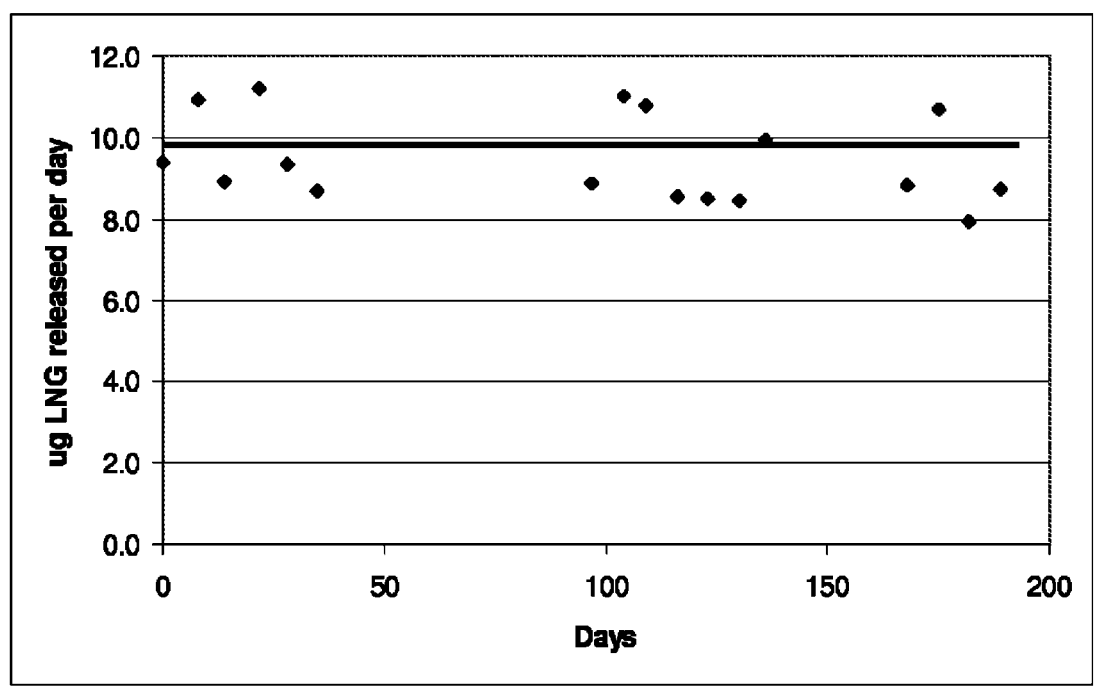
FIG. 6 illustrates the release profile of an embodiment of a delivery device using an SS-03 cylinder with type 50A silicone membrane 0.002" thick as the agent-permeable regions. As in FIG. 5, the zero time point corresponds to the equilibrium condition. Equilibrium was obtained after 63 days of soaking and subsequent LNG release values were 9-10 µg/day.

FIG. 6 illustrates release profile of the SS-03 cylinder that utilizes type 50A silicone membrane 0.002" thick. As in FIG. 5, the zero time point corresponds to the equilibrium condition. Equilibrium was obtained after 63 days of soaking and subsequent LNG release values were 9-10 μg/day.

Figure 7:
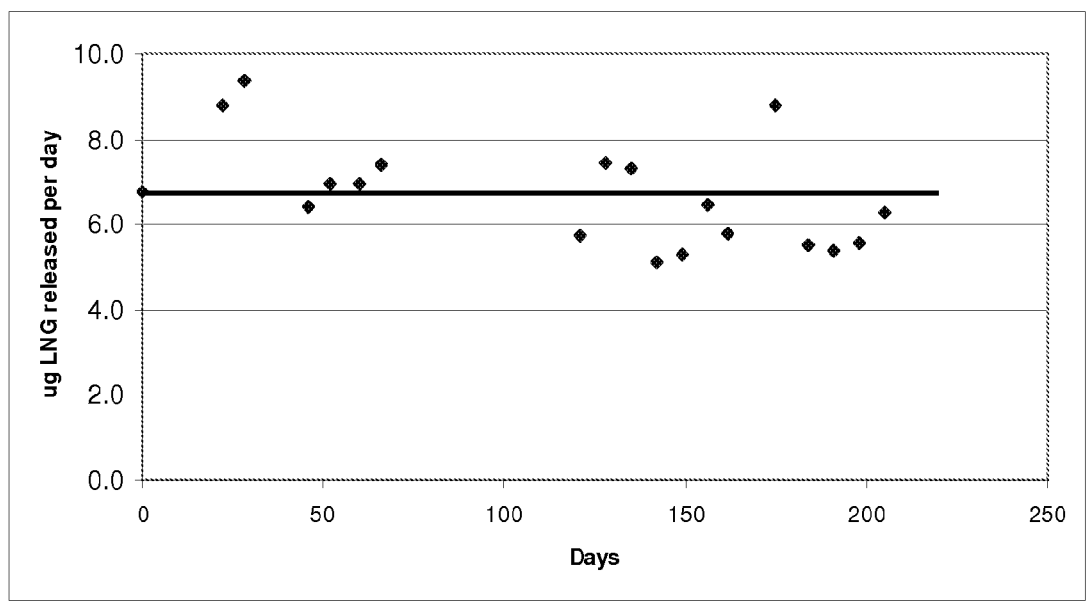
FIG. 7 illustrates the release profile of an embodiment of a delivery device using an SS-04 cartridge that utilizes type 35A silicone membrane 0.006" thick as the agent-permeable regions. As in FIGS. 5 and 6, the zero time point corresponds to the equilibrium condition. Equilibrium was obtained after 84 days of soaking and LNG release values were 6-7 µg/day.

FIG. 7 illustrates the release profile of the SS-04 cartridge that utilizes type 35A silicone membrane 0.006" thick. As in FIGS. 5 and 6, the zero time point corresponds to the equilibrium condition. Equilibrium was obtained after 84 days of soaking and LNG release values were 6-7 μg/day.

Figure 8:
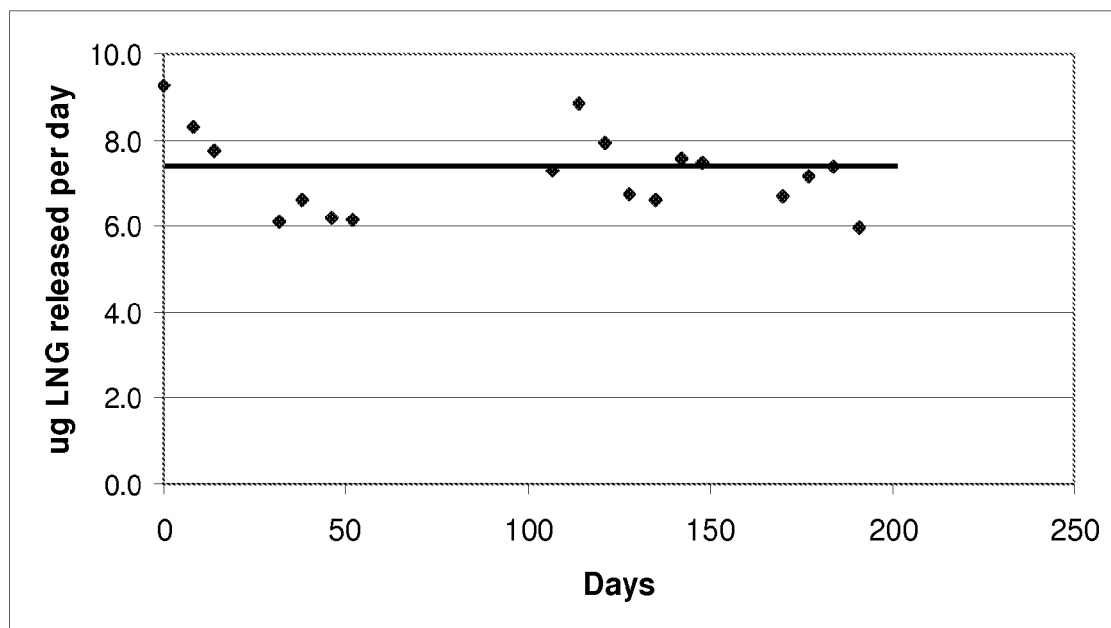
FIG. 8 illustrates the release profile of an embodiment of a delivery device using an SS-05 cartridge that utilizes type 35A silicone membranes 0.005" thick as the agent-permeable regions. As in FIGS. 5, 6 and 7, the zero time point corresponds to the equilibrium condition. Equilibrium was obtained after 84 days of soaking and LNG release values were 7-8 µg/day.

FIG. 8 illustrates the release profile of the SS-05 cartridge that utilizes type 35A silicone membranes 0.005" thick. As in FIGS. 5, 6 and 7, the zero time point corresponds to the equilibrium condition. Equilibrium was obtained after 84 days of soaking and LNG release values were 7-8 μg/day.

Table 5 summarizes the equilibration time and release amount for each of the four cylinder types.

| Silicone type | Thickness | Reference | Equilibration time | Release rate |
|---|---|---|---|---|
| 35A | 0.006" | SS-04 | 84 days | 6-7 μg/day |
| 35A | 0.005" | SS-05 | 84 days | 7-8 μg/day |
| 50A | 0.005" | SS-01 | 85 days | 7-8 μg/day |
| 50A | 0.002" | SS-03 | 63 days | 9-10 μg/day |

Equilibrium time in these examples is substantially lower (63-85 days) than observed with the Norplant® design, which takes about eighteen months.

Although the invention has been described in some detail with reference to the preferred embodiments, those of skill in the art will realize, in light of the teachings herein, that certain changes and modifications can be made without departing from the spirit and scope of the invention. Accordingly, the invention is limited only by the claims.

What is claimed is:

1. An isolated implantable chemical delivery device comprising,
    an agent-impermeable material,
    an agent reservoir disposed within the agent-impermeable material, said agent reservoir in fluid communication with one or more agent-permeable regions, said reservoir comprising a steady-state concentration of the agent that is maintained during delivery for a period of at least 30 days,
    wherein the device is a cylinder, and the cylinder body comprises the agent-impermeable material, and both ends of the cylinder comprise the agent-permeable material either through cylinder ends that are press-fit onto the cylinder body or through molded caps attached to the cylinder ends,
    wherein the device maintains a zero-order or near zero-order delivery of agent during said period.

2. The device of claim 1, wherein the agent-impermeable material is selected from ultra-high molecular weight polyethylene, polytetrafluorethylene, polypropylene, titanium, stainless steel, and polyester.

3. The device of claim 2, wherein the agent-impermeable material is ultra-high molecular weight polyethylene.

4. The device of claim 2, wherein the agent-impermeable material is steel.

5. The device of claim 1, wherein the agent-permeable material is selected from a siloxane, poly(ethylvinyl acetate), a porous membrane, an agent-impermeable material with introduced permeable imperfections, a woven material, a filtration material, and nylon.

6. The device of claim 1, wherein the agent-permeable material is polydimethylsiloxane.

7. The device of claim 1, wherein the agent-permeable material is polydimethylsiloxane with introduced imperfections.

8. The device of claim 1, wherein the device comprises a plurality of agent-permeable regions.

9. The device of claim 1, further comprising one or more perforations in the agent-impermeable material that permit no more than 25% of the total efflux of agent from the device per unit time.

10. The device of claim 1, wherein the agent reservoir comprises a saturated solution of agent and an amount of solid agent in contact with the solution.

11. The device of claim 1, wherein the agent is lipophilic and/or exhibits low aqueous solubility.

12. The device of claim 1, wherein the agent is a steroid hormone.

13. The device of claim 1, wherein the agent is levonorgestrel.

14. The device of claim 1, wherein the device provides zero-order delivery of the agent for at least 30 days.

15. The device of claim 1, wherein the device provides zero-order delivery of the agent for at least 90 days.

16. The device of claim 1, wherein the device provides zero-order delivery of the agent for at least 180 days.

17. A method of equilibrating an agent-delivery device, comprising:
    providing an agent-delivery device, said device comprising an agent-impermeable material, an agent reservoir disposed within the agent-impermeable material, said agent reservoir in fluid communication with one or more agent-permeable regions disposed within the device and accessible to the device surface, said reservoir comprising an amount of agent;
    wherein the device is a cylinder, and the cylinder body comprises the agent-impermeable material, and both ends of the cylinder comprise the agent-permeable material, either through cylinder ends that are press-fit onto the cylinder body or through molded caps attached to the cylinder ends; and
    incubating the device within a solution for a time sufficient to reach a steady state of agent concentration in the reservoir and a steady state of delivery through the agent-permeable region(s).

18. The method of claim 17, wherein the solution is selected from water, a salt solution, and a culture medium.

19. The method of claim 18, wherein the solution is phosphate-buffered saline.

20. A pre-equilibrated device produced by the method of claim 17.

21. Use of the device of claim 1 for the delivery of the agent.

* * * * *